United States Patent [19]

Bashkansky et al.

[11] Patent Number: 5,270,853
[45] Date of Patent: Dec. 14, 1993

[54] METHOD AND APPARATUS FOR IMAGING AN OBJECT IN OR THROUGH A SCATTERING MEDIUM BY USING MULTIPLE-WAVE MIXING

[75] Inventors: Mark Bashkansky; John F. Reintjes, both of Alexandria, Va.

[73] Assignee: The United States of America as represented by the Secretary of the Navy, Washington, D.C.

[21] Appl. No.: 983,334

[22] Filed: Nov. 30, 1992

[51] Int. Cl.$^5$ .................. H03F 7/00; G01B 9/021; H01S 3/10

[52] U.S. Cl. .................. 359/326; 359/334; 359/10; 359/27; 359/28; 359/34; 356/347; 385/122; 372/21

[58] Field of Search ............ 359/326, 327, 328, 332, 359/27, 28, 30, 10, 11, 34, 334, 331, 341, 346, 347; 356/347; 385/122; 372/21

[56] References Cited

U.S. PATENT DOCUMENTS

| | | | |
|---|---|---|---|
| 3,544,711 | 12/1970 | DeBitetto | 359/27 X |
| 4,178,079 | 12/1979 | Bjorklund et al. | 350/353 |
| 4,277,127 | 7/1981 | Smith | 359/10 X |
| 4,750,153 | 6/1988 | Owechko et al. | 365/125 |
| 4,796,992 | 1/1989 | Aoshima et al. | 356/347 |
| 4,879,532 | 11/1989 | Shemwell et al. | 359/27 X |
| 4,921,353 | 5/1990 | Chiou et al. | 356/347 |
| 4,945,239 | 7/1990 | Wist et al. | 250/358.1 |
| 4,948,212 | 8/1990 | Cheng et al. | 350/364 |
| 4,968,107 | 11/1990 | Yeh | 350/364 |
| 4,983,004 | 1/1991 | Takeya et al. | 359/28 X |
| 4,989,071 | 1/1991 | Hopwood | 359/28 X |
| 5,006,813 | 4/1991 | Khoshnevisan et al. | 359/326 X |
| 5,014,709 | 5/1991 | Bjelkhagen et al. | 359/10 X |
| 5,035,506 | 7/1991 | Ouhayoun | 356/349 |
| 5,071,208 | 12/1991 | Chang | 359/10 X |
| 5,140,463 | 8/1992 | Yoo et al. | 359/559 |
| 5,150,228 | 9/1992 | Liu et al. | 359/7 |
| 5,191,389 | 3/1993 | Verhoeven | 359/347 |
| 5,216,527 | 6/1993 | Sharnoff et al. | 359/347 |

OTHER PUBLICATIONS

Optical Society of American Annaul Meeting, 1991, Summaries of *Papers Presented at the Annual Meeting of the Optical Society of America*, Nov. 3-8, 1991, San Jose, Calif., 1991 Technical Digest Series, vol. 17, Postconference Edition, Abstract MZ6, M. Bashkansky and J. Reintjes, p. 28.

*Holography and four-wave mixing to see through the skin*, Hendrik J. Gerritsen, SPIE vol. 519, Analog Optical Processing and Computing (1984), pp. 128-131.

*Time-gated imaging through scattering media using stimulated Raman amplification*, M. D. Duncan, R. Mahon, L. L. Tankersley, and J. Reintjes, 1991 Optical Letters, vol. 16, No. 23, Dec. 1, 1991; 1991 Optical Society America, pp. 1868-1870.

(List continued on next page.)

*Primary Examiner*—Brian Healy
*Attorney, Agent, or Firm*—Thomas E. McDonnell; George Jameson

[57] ABSTRACT

A method and apparatus for imaging an object that is part of, embedded in, or viewed through a scattering medium is provided. A broadband stochastic beam generator, such as a broadband laser, generates a broadband stochastic beam and a narrowband beam generator generates a narrowband beam. A non-linear mixing crystal receives the broadband stochastic beam and the narrowband beam and provides a signal light beam conjugate correlated with the broadband stochastic beam to the scattering medium. A multiple-wave mixing cell is disposed to receive the signal light beam from the scattering medium. An adjustable delay path also illuminates the multiple-wave mixing cell with the broadband stochastic beam. A supplemental beam generator is also provided for also additionally illuminating the multiple-wave mixing cell with a supplemental beam having characteristics sufficient to satisfy phase matching with the material of the multiple-wave mixing cell. The multiple-wave mixing cell produces an image-bearing beam which contains an image of an object extracted from the signal light beam emitted from the scattering medium. The apparatus can further include a detector to record the image of the object in the image-bearing beam.

26 Claims, 3 Drawing Sheets

OTHER PUBLICATIONS

*Chrono–Coherent Imaging for Medicine*, Kenneth G. Spears, Jenifer Serafin, Nils H. Abramson, Xinming Zhu, and Hans Bjelkhagen, IEEE Transactions on Biomedical Engineering, vol. 36, No. 12, Dec. 1989, pp. 1210–1221.

*Controlled picosecond gating and amplification of ultrafast optical signals*, G. L. Olson and G. E. Bush, Applied Physics Letters, vol. 27, No. 12, Dec. 15, 1975, pp. 684–686.

*Picosecond-gated optical amplifier*, G. E. Busch, K. S. Greve and G. L. Olson; R. P. Jones and P. M. Rentzepis, Applied Physics Letters, vol. 27, No. 8, Oct. 15, 1975, pp. 450–452.

*Time–resolved transillumination for medical diagnostics*, S. Andersson-Engels, R. Berg, and S. Svanberg, O. Jarlman, Optics Letters, vol. 15, No. 21, Nov. 1, 1990, pp. 1179–1181.

*Electronic holography and speckle methods for imaging through tissue using femtosecond gated pulses*, E. Leith, H. Chen, Y. Chen, D. Dilworth, J. Lopez; R. Masri, Jo Rudd and J. Valdmanis, Applied Optics, vol. 30, No. 29, Oct. 10, 1991, pp. 4204–4210.

*An Optical Up-Conversion Light Gate With Picosecond Resolution*, H. Mahr and Mitchell D. Hirsch, Optics Communications, vol. 13, No. 2, Feb. 1975, pp. 96–99.

*Two–dimensional imaging through diffusing media using 150–fs gated electronic holography techniques*, H. Chen, Y. Chen, D. Dilworth, E. Leith, J. Lopez and J. Valdmanis, 1991 Optical Society of America, vol. 16, No. 7, Apr. 1, 1991, pp. 487–489.

METHOD AND APPARATUS FOR IMAGING AN OBJECT IN OR THROUGH A SCATTERING MEDIUM BY USING MULTIPLE-WAVE MIXING

CROSS-REFERENCE TO RELATED APPLICATIONS

This application is related to commonly assigned, U.S. application Ser. No. 07/861,213, pending, filed on Mar. 31, 1992 by Reintjes, Duncan, Mahon, Tankersly, Waynant and Bashkansky and entitled "Time-Gated Imaging Through Dense-Scattering Materials Using Stimulated Raman Amplification" and commonly assigned, U.S. application Ser. No. 07/970,886, pending, filed on Nov. 3, 1992 by Bashkansky and Reintjes and entitled "Apparatus For Imaging An Object In Or Through A Scattering Medium Using Coherent Anti-Stokes Raman Scattering", which are incorporated herein by reference.

BACKGROUND OF THE INVENTION

1. Field of the Invention

The present invention relates to imaging devices and, more particularly, to a method and apparatus for imaging an object in or through a scattering medium using a non-linear mixing crystal and a multiple-wave multiple-wave mixing cell.

2. Description of the Related Art

Images of objects that are part of, embedded in, or viewed through a medium in which a significant amount of multiple path scattering occurs are usually blurred or otherwise degraded in resolution or completely obscured because the different paths over which the scattered radiation travels causes the image to appear to arise from more than one location within the scattering medium. FIG. 1 illustrates a scattering medium illuminated by a light beam 60. When the light beam 60 travels through the scattering medium 10, the light is scattered and emitted as beam 65. There are several methods that can be used to overcome this problem, with each having certain disadvantages.

A first method involves the spatial filtering of the image to include only those rays that are not deviated too far from the axis of the optical system. This technique fails to effectively eliminate the background radiation due to the scattered light.

A second method of overcoming the blurring of the image is to time gate the transmitted signal so that only the earliest light that emerges from the scattering medium is recorded by a detector. This "first light" either is not scattered, or is scattered over a relatively short path compared to light that emerges later, and therefore provides the least amount of image degradation. Imaging through dense scattering materials, such as biological tissue, or solids or liquids that appear translucent or even opaque to the unaided eye can require gating times of the order of 10 picoseconds or less.

There are several techniques currently used to perform such time-gated imaging measurements, including various forms of electronic gating and optical gating. Electronic gating can be accomplished either by gating a photoelectric image tube directly, or by switching some other part of the photoelectric detection circuit. These techniques are currently limited to gating times of the order of 50–100 picoseconds (psec) or longer.

Another technique involves the use of picosecond or femtosecond pulses for illumination of the object, followed by an optical gating technique to provide the time resolution. Such techniques can provide time gates in the picosecond or subpicosecond regime, depending on the length of the optical pulse.

One gating technique suitable for picosecond or femtosecond pulses is holography. Conventional holography, or electronic holography, can be used. However, all of the transmitted light is recorded at the detector. If a large fraction of the transmitted light is contained in the non-image bearing tail that is delayed through scattering, the interference fringes that form the hologram will be washed out, and the noise in the image will be increased until the image is totally obscured.

Holography can also be accomplished with broadband, long-pulse laser light, in which the gate time is determined by the inverse of the bandwidth of the light. However, this technique suffers from the same disadvantages described above for picosecond holography: large signal requirements and relatively low contrast between the image-bearing portion of the transmitted light and the non-image-bearing tail.

Another technique for short pulse gating is the use of a Kerr shutter, in which the transmission of light through a cell between crossed polarizers is controlled by a second pulse of light. The gate times for this approach can be of the order of picoseconds, depending on the duration of the controlling light pulse and the response time of the active medium in the Kerr gate. This technique suffers from limitations in contrast because of leakage of the wrong polarization through the polarizers, and losses in the Kerr gate because the transmission is less than 100%.

Image amplification with picosecond time-gated amplifiers based on dye amplifiers pumped by picosecond laser pulses have also been described in the prior art. The limitations of these amplifiers are that the high level of fluorescence necessary to produce the short gating time contributes a background on top of the amplified image, limiting the sensitivity and increasing the noise level.

Several other techniques are also possible. Streak cameras can be used to record the image. Time resolutions down to 2 picoseconds are currently possible. However, only a one-dimensional image is obtained, requiring scanning to produce a two-dimensional image. In addition, the streak cameras are of limited sensitivity, limiting their utility in detecting low-level signals. Another approach that uses time-gating involves the technique of four-wave mixing. Conversion of the signal light takes place only while the gating pulse is present. The main drawback to this approach is the combination of low conversion efficiencies associated with the conversion process (10% or less), coupled with limitations on the allowable illumination signal as set by the ANSI standards for irradiation of living tissue. Four-wave mixing using phase conjugation has also been suggested. The disadvantage of this technique is that, while phase conjugation can correct refractive distortion, it does not correct for scattering distortion due to fundamental considerations.

Non time-gating techniques also include the use of holographic recordings using spatial correlation to discriminate against the non image-bearing light. This approach has the same limitations due to low contrast with non-correlated light as discussed above for holography. Finally, use may be made of absorption in the sample to attenuate the longer paths associated with the multiple scattered light. This can work in materials that are highly absorbing, but not for materials that are primarily scattering rather than absorbing.

Recently developed systems involve time gating by stimulated Raman amplification using short light pulses, and correlation gating using coherent Anti-Stokes Raman scattering.

None of the above-described systems minimizes the scattered background without introducing noise, while simultaneously operating at high efficiency with long laser pulses.

SUMMARY OF THE INVENTION

It therefore an object of the present invention to provide a method and apparatus for imaging an object that is embedded in or viewed through a scattering medium using long duration pulses.

Another object of the present invention is to provide a method and apparatus for imaging an object that is embedded in or viewed through a scattering medium which provides both short time resolution and long duration pulse light illumination to the scattering medium.

Another object of the present invention is to provide a method and apparatus for imaging an object that is embedded in or viewed through a scattering medium capable of eliminating photon noise in addition to removing background illumination due to scattering within the scattering medium.

Another object of the present invention is to provide a method and apparatus for imaging an object that is embedded in or viewed through a scattering medium capable of effectively removing background illumination caused by scattering within the scattering medium and still provide an extracted image of sufficient intensity and quality.

A further object of the present invention is to provide a method and apparatus for optically extracting an object in a beam of light emitted from a scattering medium.

In order to achieve the foregoing and other objects, in accordance with the purposes of the present invention as described herein, a method and apparatus for imaging an object that is embedded in or viewed through a scattering medium is provided. A broadband stochastic beam generator, such as a broadband pulse laser, generates a broadband stochastic beam and a narrowband beam generator generates a narrowband beam. A non-linear mixing crystal receives the broadband stochastic beam and the narrowband beam and provides a signal light beam to the scattering medium at a frequency equal to the difference between the frequency of the narrowband beam and the broadband stochastic beam. A cell is disposed to receive the signal light beam from the scattering medium. An adjustable delay path also illuminates the multiple-wave mixing cell with the broadband stochastic beam. A supplemental beam generator is also provided for additionally illuminating the multiple-wave mixing cell with a supplemental beam having characteristics sufficient to satisfy phase matching with the material of the multiple-wave mixing cell. The multiple-wave mixing cell produces a image-bearing beam which contains an image of an object extracted from the signal light beam emitted from the scattering medium.

The above-mentioned and other objects of the present invention will become more apparent from the following description when read in conjunction with the accompanying drawings. However, the drawings and descriptions are merely illustrative in nature and not restrictive.

DESCRIPTION OF THE PREFERRED EMBODIMENT

Figure 1:
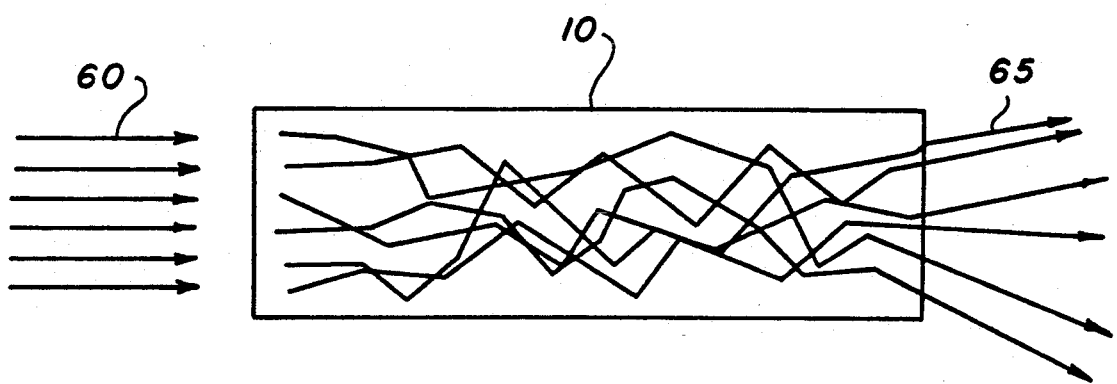
FIG. 1 illustrates a diagram of a scattering medium.
Figure 2:
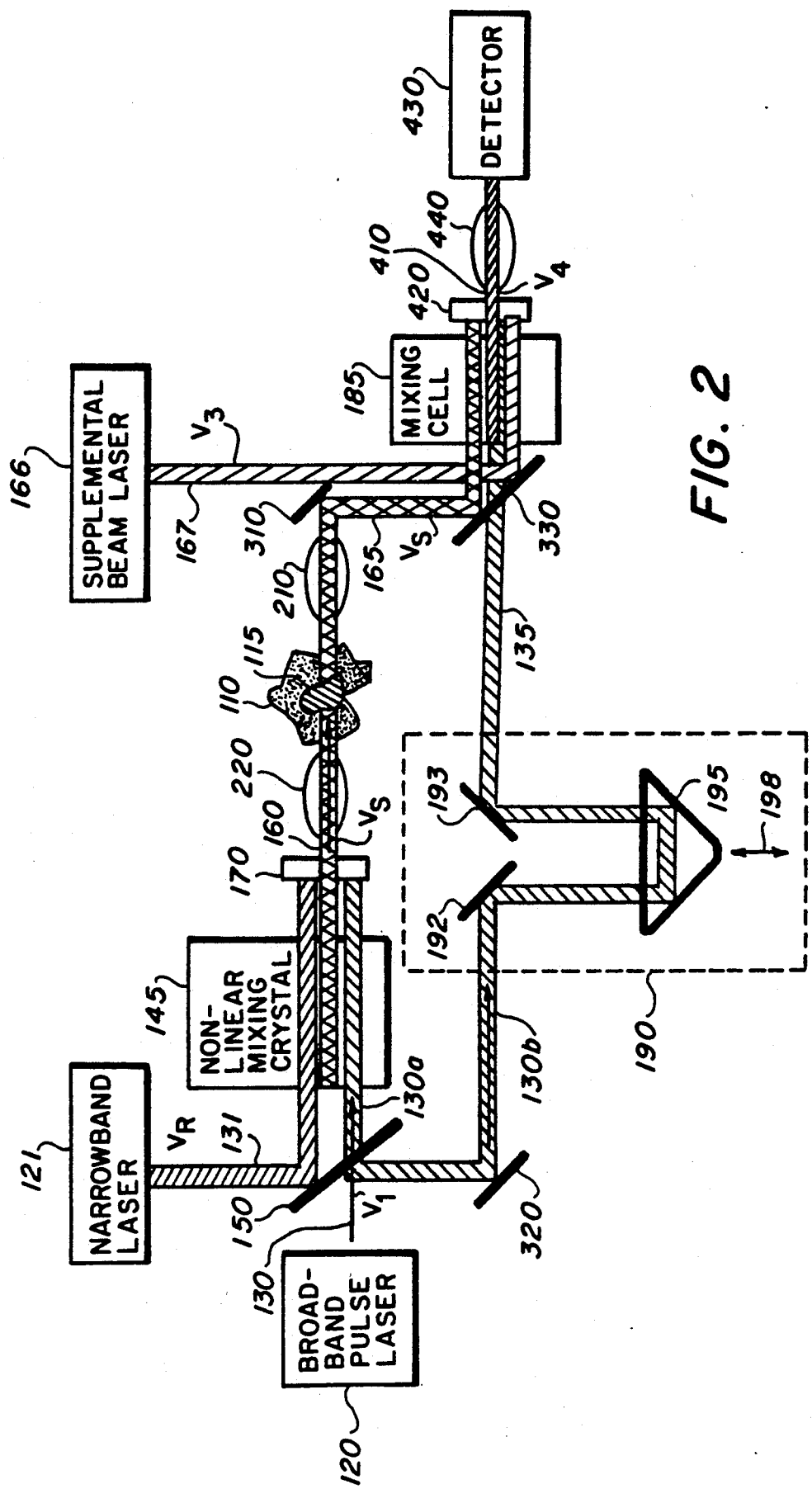
FIG. 2 illustrates a schematic block diagram of the method and apparatus for imaging an object embedded in or viewed through a scattering medium according to a preferred embodiment of the present invention.

FIG. 2 illustrates a method and apparatus according to a preferred embodiment of the present invention for imaging an object embedded in or viewed through a scattering medium 110. A broadband pulse laser 120 can provide a broadband stochastic beam 130. The broadband pulse laser 120 can provide long duration pulses of at least about one nanosecond ($10^{-9}$ seconds). A relatively small portion 130a of the broadband stochastic beam 130 output of the broadband pulse laser 120 is passed through a beam splitter 150 to illuminate a non-linear mixing crystal 145 and the remaining larger portion 130b of the beam 13 is reflected by a beam splitter 150.

A narrowband laser 121 provides a narrowband beam 131 for also illuminating the non-linear mixing crystal 145. The narrowband laser 121 can be a conventional pulse laser having a pulse duration comparable to that of the laser 120, as discussed above. Additionally, the pulses of the narrowband laser 121 must be synchronized with the pulses of the broadband pulse laser 120. However, the narrowband laser 121 can also, alternatively, be a conventional continuous wave coherent laser or the like and not provide pulses.

The non-linear mixing crystal 145 should preferably be made of materials sufficient to provide the signal light beam 160 by three wave difference frequency mixing of the light from the broadband stochastic beam 130 output of the broadband pulse laser 120. These materials can be, for example, potassium titanyl phosphate, potassium dihydrogen phosphate or lithium niobate. However, the narrowband laser 121 and the non-linear mixing crystal 145 can be eliminated altogether if replaced by a light source that is conjugate correlated with the broadband stochastic beam 130a and of a frequency $\nu_S$ different from a two photon transition frequency $\nu_R$ by a frequency $\nu_1$ of the broadband stochastic beam 130a.

The non-linear mixing crystal 145 provides a signal light beam 160 that is correlated with the complex conjugate of the light in the broadband stochastic beam 130a. The frequency of the signal light beam 160, $\nu_S$, is the frequency difference between the frequency $\nu_1$ of the broadband stochastic beam 130a and the frequency $\nu_R$ of the narrowband beam 131, i.e. $\nu_S = \nu_R - \nu_1$.

A filter 170 passes the signal light beam 160 and blocks the broadband stochastic beam 130a and the narrowband beam 131 which emerge from the non-linear mixing crystal 145. Alternatively, polarization filters can be used instead of frequency filtering to remove the broadband stochastic beam 130a and the narrowband beam 131 and pass the signal light beam 160. Further, although it is preferred that both the broadband stochastic beam 130a and the narrowband beam 131 illuminate an entirety of the non-linear crystal 145, it is possible that the beams 130a and 131 can illuminate the non-linear mixing crystal 145 at different angles. In such an instance, the signal light beam 160 may be passed out of the non-linear mixing crystal 145 at a different angle than the beams 130a and 131. In such a case, the signal light beam 160 can be captured for elimination of the scattering medium 110.

The signal light beam 160 scatters within the scattering medium 110 to produce a signal light beam 165 which is then projected upon a multiple-wave mixing cell 185. The portion 130b of the broadband stochastic beam 130 that is reflected by the beam splitter 150 is passed through an adjustable reference path 190 to produce a delayed broadband stochastic beam 135, which is also directed into the multiple-wave mixing cell 185. Further, a supplemental beam laser 166 generates a supplemental beam 167 for illumination of the multiple-wave mixing cell 185. Because the multiple-wave mixing cell 185 receives three waves (165, 135 and 167) and generates a fourth wave or image-bearing beam 410 in the illustrated embodiment, it is often referred to as a four-wave or a multiple-wave mixing cell. When the multiple-wave mixing cell 185 is formed of a material having a two photon transition at the frequency $\nu_R$ of the narrowband laser 121, the image-bearing beam 410 contains an image of the object 115, that is embedded in or viewed through the scattering medium 110, without distortions from scattering and without additional photon noise from the multiple wave mixing process.

The multiple-wave mixing cell 185 can be an atomic vapor that is a metallic vapor such as, for example, barium. Other possible metallic vapors include strontium, rubidium and cesium. The multiple-wave mixing cell 185 can be any material having a narrow band two photon transition (resonance) at the frequency $\nu_R = \nu_1 + \nu_S$ wherein $\nu_1$ is the frequency of the broadband stochastic beam 130b, $\nu_S$ is the frequency of the signal light beam 160 and $\nu_R$ is the frequency of the narrowband beam 131. This two photon resonance should have a bandwidth transition that is small compared to the bandwidth of the broadband stochastic beam 130b and the signal light beam 160. Because the available lasers for providing a desirable frequency and intensity of a signal light beam are limited by nature, the materials for the multiple-wave mixing cell having convenient two photon resonance are limited.

For example, when barium having a two photon transition wavelength $1/\nu_R = \lambda_R$ of 433.61 nanometers is used for the multiple-wave mixing cell 185 and when the scattering medium 110 conveniently can be imaged by a signal light 160 of a wavelength $1/\nu_S = \lambda_S$ of 850 nanometers, then the broadband stochastic beam 130a should have a frequency of $1/\nu_1 = \lambda_1 = 885.16$ nanometers. The supplemental beam 167 can thus be chosen at $1/\nu_3 = \lambda_3 = 750$ nanometers so that the image-bearing beam 410 is at $1/\nu_4 = \lambda_4 = 274.8$ nanometers.

The supplemental beam laser 166 can be either a broadband or narrowband laser capable of emitting light of a frequency sufficient to satisfy phase matching requirements with the material of the multiple-wave mixing cell 185. The frequency $\nu_3$ of the supplemental beam 167 generated by the supplemental beam laser 166 should be chosen so that phase matching conditions in the multiple-wave mixing cell 185 are satisfied for the sum frequency process $\nu_4 = \nu_1 + \nu_S + \nu_3$. The supplemental beam laser 166 can be either a pulse laser or a continuous wave coherent laser. However, if the supplemental beam laser 166 is a pulse laser, it must be synchronized with pulses of the broadband pulse laser 120.

When the appropriate frequencies causing the excitations discussed above are chosen, the multiple-wave mixing cell 185 causes performance of a correlation function on the beams 135 and 165 and produces the image-bearing beam 410. The correlation performed in the multiple-wave mixing cell 185 produces the image-bearing beam 410 at an intensity I proportional to an integral of the laser amplitude $A_1$ correlated with the signal light beam $A_S$ with respect to time, according to the following relations:

$$I \propto |\int A_1(t) A_S(t) dt|^2$$

$$A_S(t) \propto A_1^*(t-\tau)$$

When the frequency of narrowband beam 131 matches a two photon resonance in the material in mixing cell 185, the correlation function described above will be performed and the intensity of the image-bearing beam 410 will be maximum.

The signal light beam 165 provided from the scattering medium 110 to the multiple-wave mixing cell 185 can be directed at an angle or parallel with respect to the broadband stochastic beam 130 and the supplemental beam 167. Furthermore, the signal light beam 165, the broadband stochastic beam 135 and the supplemental beam 167 preferably should illuminate the same portion of the multiple-wave mixing cell 185. It is preferable that the size of the beams 135, 165 and 167 illuminate a totality of the multiple-wave mixing cell 185 by adjustment therewith using various conventional optics such as a lens or optical train 210 disposed, for example, between the object 115 and the multiple-wave mixing cell 185. An optical train 220, such as a telescope or lens combination, can also be provided between the filter 170 and the scattering medium 110 to adjust the beam width of the signal light beam 160 provided to the scattering medium 110. Further, as can be appreciated, various conventional mirrors 310 and 320 and a beam splitter 330 are preferable for directing the beams. For example, the mirror 310 could be positioned to reflect the beam 165 from the optical train 210 off of the beam splitter 330 into the mixing cell 185. In a like manner, the mirror 320 could be positioned to reflect the beam 130b from the beam splitter 150 into the adjustable reference path 190. The beam splitter 330 enables superposition of the broadband stochastic beam 135 and the signal light beam 165 on the multiple-wave mixing cell 185. The order of the mirrors 310 and 320, the beam splitter 330 and lenses such as the optical train 210 is not important.

The image-bearing beam 410 is produced within the multiple-wave mixing cell 185. The beam 410 contains image information on an object 115 without defects due to scattering in the scattering medium. The defects in the signal light beam 165 are absent in the image-bearing beam 410 when a reference beam provided by the broadband pulse laser 120 is properly distanced from the multiple-wave mixing cell 180 by the adjustable reference path 190 as discussed below.

Besides the frequencies of the beams, the adjustable reference path 190 adjusts a pathlength of the broadband stochastic beam 130 provided by the broadband pulse laser 120. The pathlength depends upon characteristics such as the length of the scattering medium 110 in order to produce the image-bearing beam 410 in the multiple-wave mixing cell 185 so that the image-bearing beam 410 represents an object 115 in the scattering medium 110 without distortions therein. A pathlength of the adjustable reference path 190 is adjusted to vary the arrival at the multiple-wave mixing cell 185 of the pulses in the beams 135 and 165. A relative timing between the beams 135 and 165 should be chosen so as to cause the pulses to overlap in time in the multiple-wave mixing cell 185.

The adjustable reference path 190 preferably contains mirrors 192 and 193 and a retroreflector 195 such as a corner cube or rooftop prism. The retroreflector 195 is translatable in the directions of double-arrows 198. Translation of the retroreflector 195 can adjust the pathlength and thus the timing of the broadband stochastic beam 135. Typically, the rooftop prism, for example, is mounted on a translatable stage moved by, for example, a screw or electric motor (not shown) to thus shorten or length the optical path through the adjustable reference path 190.

A filter 420 is preferably used to pass the image-bearing beam 410 and block all three of the broadband stochastic beam 135, the signal light beam 165 and the supplemental beam 167. The filter 420 can be sensitive to frequency or alternatively can be replaced with polarization filters to pass the image-bearing beam 410 and remove the beams 135, 165 and 167. A conventional detector 430, such as a charge coupled array device (CCD) array, a two-dimensional photo detector or a scanning one-dimensional photodetector array, receives the image-bearing beam 410 to detect an image of the object 115 or the like in the scattering medium 110. Thus, it is possible to use a light beam to image an object 115 embedded in or viewed through a scattering medium 110 even though the light beam is scattered within the scattering medium 110 to obstruct optical viewing of the object 115 by the naked eye or other conditionally known imaging techniques.

It is possible that the phase matching conditions in mixing cell 185 can be satisfied if the beams 135, 165, 167 and 410 pass through the cell 185 at different angles. Thus, it is also possible that a filter can be avoided altogether and the detector 430 placed at an angle sufficient to receive the image-bearing beam 410 and not receive the other three beams 135, 167 and 165. Further, optics such as the illustrated lens 440 can also be utilized between the filter 420 and the detector 430 to adjust the size of the image-bearing beam 410 to the size of the detector 430.

The type of broadband pulse laser 120 is not important and any conventional laser will do so long as it is capable of delivering pulses of broadband stochastic light. However, the broadband pulse laser 120 can be a dye laser or a solid state laser made of, e.g., titanium sapphire, alexandrite, Li:CAF or Li:SAF. When barium is used for the multiple-wave mixing cell 185, in the above example, the broadband pulse laser 120 preferably has a wavelength $1/\nu_1 = \lambda$ of 885.16 nanometers with a total bandwidth of about 10 nanometers. The broadband pulse laser 120 preferably produces long pulses of at least about one nanosecond ($10^{-9}$ seconds). A long pulse is preferred for viewing tissue to avoid exceeding maximum permissible exposure levels established by the American National Standards Institute (ANSI) tissue illumination standards.

Theoretical studies have shown that the use of the multiple-wave mixing cell 185 with the two photon resonance described above will produce the image-bearing beam 410 with no added photon noise because of the fundamental nature of the interaction in the multiple-wave mixing cell 185.

Figure 3:
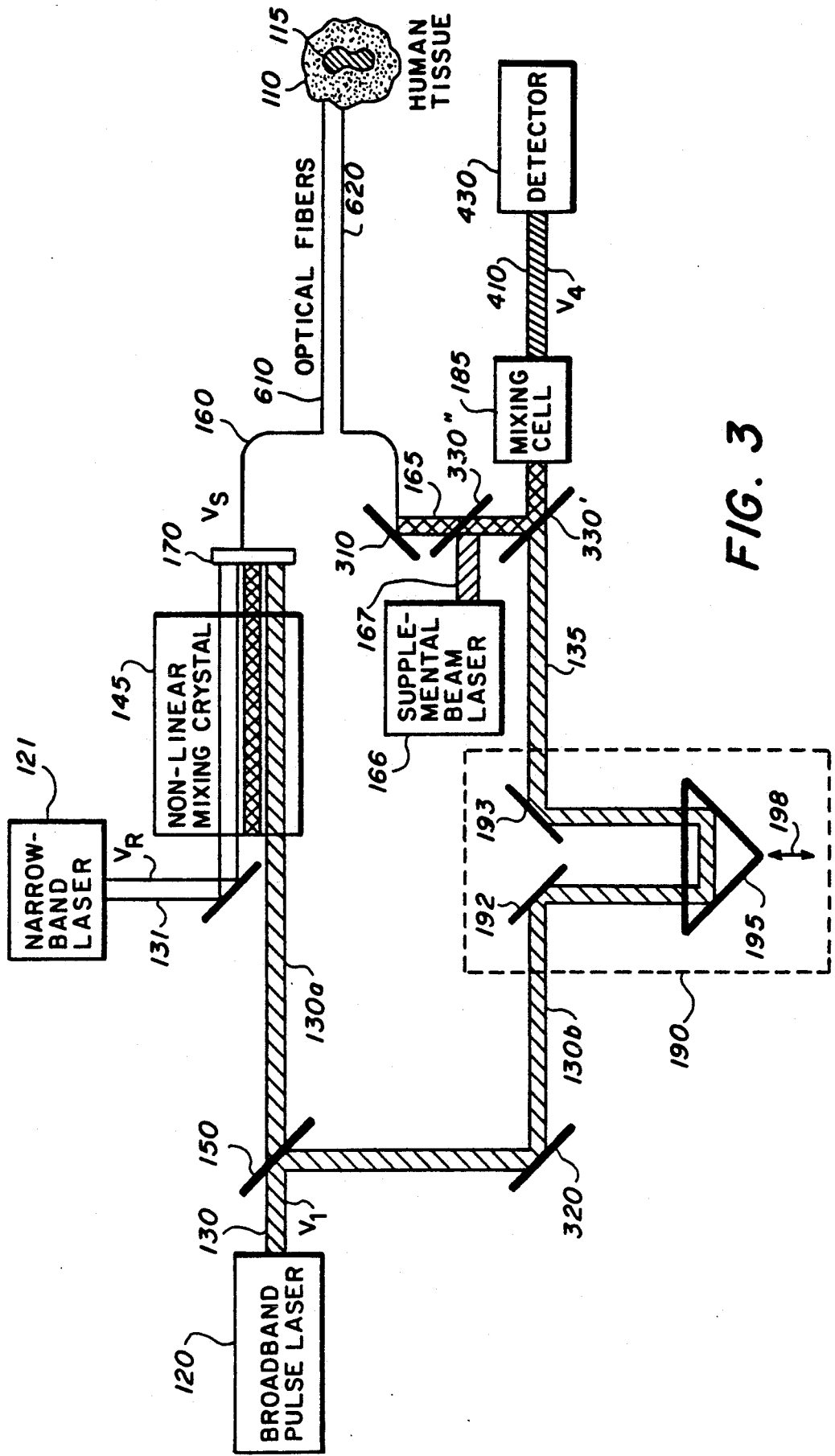
FIG. 3 illustrates a modification of the embodiment of FIG. 2.

FIG. 3 illustrates a modification of the embodiment of FIG. 2, wherein like elements are illustrated with like reference numerals. In FIG. 3, the signal light beam 160 is reflected from the scattering medium 110 to produce the beam 165. As shown in FIG. 3, optical fibers 610 and 620 are used to deliver the beams to and from the scattering medium 110. The optical fibers 610 and 620 can be of any length for imaging tissue, such as a prostate, for example, within a human body.

While the invention has been illustrated and described in detail in the drawings and foregoing descriptions, it will be recognized that any changes and modifications will occur to those skilled in the art. For example, laser 120 could produce short pulses of the order of an exemplary one picosecond (1 psec). With short pulse operation of laser 120, laser 121 could also produce short pulses of comparable duration. Under such short pulse operation, it is further possible that the nonlinear mixing crystal 145 could be eliminated and the signal beam 160 could be obtained from a separate short pulse laser. Under these alternatives, the pulses in beam 135 and in the unscattered part of beam 165 should arrive in synchronism at the mixing cell 185. In a further alternative, it could be possible to derive the conjugate correlated beam 160 from a separate broadband long pulse laser, eliminating the need for mixing crystal 145 and the narrowband laser 121. It is therefore intended by the appended claims, to cover such changes and modifications as fall within the true spirit and scope of the invention.

What is claimed and desired to be secured by Letters Patent of the United States is:

1. An apparatus for imaging an object that is part of, embedded in, or viewed through a scattering medium, said apparatus comprising:
  a broadband stochastic beam generator for providing a broadband stochastic beam;
  a signal light beam generator for providing a signal light beam conjugate correlated with the broadband stochastic beam;
  means for receiving the signal light beam after dispersion in the scattering medium and the broadband stochastic beam from the broadband stochastic beam generator, said receiving means formed of a material having a two photon transition frequency higher than a frequency of the signal light beam; and
  a supplemental beam generator for applying a supplemental beam to said receiving means with characteristics sufficient to satisfy phase matching with the material of said receiving means, said receiving means being responsive to the signal light beam after dispersion in the scattering medium, the broadband stochastic beam and the supplemental beam for producing an image-bearing beam containing an image of the object in the scattering medium.

2. The apparatus of claim 1 wherein said receiving means comprises:
  a multiple-wave mixing cell.

3. The apparatus of claim 1 wherein:
  said broadband stochastic beam generator comprises a broadband pulse laser.

4. The apparatus of claim 1 wherein:

said broadband stochastic beam generator comprises a long pulse laser.

5. The apparatus of claim 1 wherein said signal light beam generator comprises:
a narrowband beam generator for generating a narrowband beam; and
means responsive to the broadband stochastic beam and the narrowband beam for providing to the scattering medium the signal light beam as a conjugate correlation with the broadband stochastic beam, the conjugate correlation including a frequency difference.

6. The apparatus of claim 5 wherein:
said providing means comprises a non-linear mixing crystal.

7. The apparatus of claim 6 wherein:
said receiving means comprises a multiple-wave mixing cell.

8. The apparatus of claim 1 further comprising:
a detector responsive to the image-bearing beam for recording an image of the object in the scattering medium.

9. The apparatus of claim 7 further comprising:
a detector responsive to the image-bearing beam for recording an image of the object in the scattering medium.

10. The apparatus of claim 7 wherein:
said narrowband beam generator has characteristics sufficient to generate the narrowband beam at a frequency essentially equal to the two photon transition frequency of the material of said multiple-wave mixing cell.

11. The apparatus of claim 7 wherein:
said non-linear mixing crystal comprises a material selected from the group consisting of potassium titanyl phosphate, potassium dihydrogen phosphate and lithium niobate.

12. The apparatus of claim 7 wherein:
said non-linear mixing crystal consists of potassium titanyl phosphate.

13. An apparatus according to claim 7 wherein:
said non-linear mixing crystal consists of potassium dihydrogen phosphate.

14. The apparatus of claim 7 wherein:
said non-linear mixing crystal consists of lithium niobate.

15. The apparatus of claim 2 wherein:
the material of said multiple-wave mixing cell has the two photon transition frequency essentially equal to a sum of the frequency of the signal light beam and a frequency of the broadband stochastic beam.

16. The apparatus of claim 2 wherein:
said multiple-wave mixing cell comprises an atomic vapor.

17. The apparatus of claim 15 wherein:
said multiple-wave mixing cell comprises a metallic vapor selected from the group consisting of barium, strontium, rubidium and cesium.

18. The apparatus of claim 15 wherein:
said multiple-wave mixing cell comprises barium.

19. The apparatus of claim 15 wherein:
said multiple-wave mixing cell comprises strontium.

20. The apparatus of claim 7 further comprising:
a filter optically disposed between said non-linear mixing crystal and the scattering medium, said filter having characteristics sufficient to pass the signal light beam and to block the broadband stochastic beam and the narrowband beam.

21. The apparatus of claim 3 further comprising:
an adjustable optical path length optically disposed between said broadband stochastic beam generator and said multiple-wave mixing cell.

22. The apparatus of claim 2 wherein:
said multiple-wave mixing cell produces a image-bearing beam at an angle different than that of each of the broadband stochastic and signal light beams; and
wherein said apparatus further comprises a detector optically disposed along the angle to detect the image-bearing beam and avoid the broadband stochastic and signal light beams.

23. The apparatus of claim 2 further comprising:
an output filter optically disposed at an optical output of the multiple-wave mixing cell, said an output filter having characteristics sufficient to block both the broadband stochastic beam and the narrowband stochastic beam and to pass a image-bearing beam generated within said multiple-wave mixing cell.

24. The apparatus of claim 1 further comprising:
at least two parallelly arranged fiber optical cables, one fiber optical cable optically disposed to guide the signal light beam to the scattering medium and another fiber optical cable optically disposed to guide the signal light beam reflected from or transmitted through the scattering medium.

25. An apparatus for imaging an object that is part of, embedded in or viewed through a scattering medium, said apparatus comprising:
beam generating means for generating a broadband stochastic beam, a supplemental beam and a signal light beam conjugate correlated with the broadband stochastic beam;
multiple-wave mixing means responsive to the signal light beam after dispersion in the scattering medium, the broadband stochastic beam and the supplemental beam for performing a two photon resonant four wave sum frequency interaction to produce an image-bearing beam containing an image of the object in the scattering medium; and
means responsive to the image-bearing beam for recording an image of the object in the scattering medium.

26. A method for imaging an object that is part of, embedded in or viewed through a scattering medium, said method comprising the steps of:
(a) generating a broadband stochastic beam;
(b) generating a signal light beam conjugate correlated with the broadband stochastic beam;
(c) illuminating the object in the scattering medium with the conjugate correlated signal light beam;
(d) generating a supplemental beam;
(e) performing a two photon resonant four wave sum frequency interaction in response to the signal light beam from the scattering medium, the broadband stochastic beam, and the supplemental beam to produce an image-bearing beam containing an image of the object in the scattering medium; and
(f) detecting the image of the object in the image-bearing beam.

* * * * *